United States Patent [19]

Wu et al.

[11] 4,217,287

[45] Aug. 12, 1980

[54] EPOXIDATION OF ALPHA-OLEFINS

[75] Inventors: Ching-Yong Wu, O'Hara Township, Allegheny County; Harold E. Swift, Gibsonia; John E. Bozik, Plum Borough, all of Pa.

[73] Assignee: Gulf Research & Development Company, Pittsburgh, Pa.

[21] Appl. No.: 932,906

[22] Filed: Aug. 11, 1978

Related U.S. Application Data

[63] Continuation-in-part of Ser. No. 637,267, Dec. 3, 1975, abandoned, which is a continuation of Ser. No. 187,138, Oct. 6, 1971, abandoned, which is a continuation-in-part of Ser. No. 816,817, Apr. 16, 1969, abandoned.

[51] Int. Cl.$^2$ .......................................... C07D 301/20
[52] U.S. Cl. ................................................ 260/348.29
[58] Field of Search .................................... 260/348.29

[56] References Cited

U.S. PATENT DOCUMENTS

| | | | |
|---|---|---|---|
| 3,187,055 | 6/1965 | Armstrong et al. | 528/57 |
| 3,351,635 | 11/1967 | Kollar | 260/348.29 |
| 3,526,645 | 9/1970 | Vangermain et al. | 260/348.29 |

FOREIGN PATENT DOCUMENTS 676772  8/1952  United Kingdom.

OTHER PUBLICATIONS

Wu et al., Jour. Catalysis, vol. 43 (1976), pp. 380-383.

*Primary Examiner*—Norma S. Milestone

[57] ABSTRACT

A process for epoxidizing an alpha-olefin by adding an alpha-olefin and an oxygen transfer catalyst to a hydroperoxide stabilized with barium oxide.

18 Claims, No Drawings

EPOXIDATION OF ALPHA-OLEFINS

The application is a continuation-in-part of our patent application Ser. No. 637,267, filed Dec. 3, 1975, now abandoned, which is a continuation of Ser. No. 187,138, filed Oct. 6, 1971, now abandoned, which was a continuation-in-part of Ser. No. 816,817, filed Apr. 16, 1969, now abandoned.

This invention relates to a novel method for the epoxidation of alpha-olefins and more particularly it relates to an epoxidation process in which an alpha-olefin containing an oxygen transfer catalyst is added to a hydroperoxide stabilized with barium oxide.

It is known that olefins can be catalytically oxidized to the corresponding oxirane compound by adding an organic hydroperoxide to an excess of olefin in the presence of a suitable epoxidation catalyst provided that the olefin is sufficiently reactive and the hydroperoxide is moderately stable. It is believed that the epoxidation catalyst, also called the oxygen transfer catalyst, assists in the transfer of the oxygen from the hydroperoxide to the double bond of the olefin. In carrying out this reaction it has been known that there must be a substantial excess of olefin in the presence of the hydroperoxide in the reaction zone in order to increase the rate of olefin epoxidation and at the same time to prevent an extensive decomposition of the hydroperoxide. U.S. Pat. No. 3,351,635 discloses this use of a substantial excess of the olefin as the normal procedure for the reaction and U.S. Pat. No. 3,526,645 describes the slow addition of the organic hydroperoxide to an excess of the olefin as being the preferred procedure.

Any nonselective decomposition of the hydroperoxide lowers the selectivity of the reaction to epoxide based on the hydroperoxide converted. It is believed that the oxygen transfer catalyst catalyzes the decomposition of the hydroperoxide as an undesired side effect, which effect is particularly evident when sufficient olefin is not present in the reaction zone to accept the oxygen. Thus, the prior art suggests that the epoxidation of olefins with the organic hydroperoxides be carried out in a substantial excess of the olefin by adding less than the stoichiometric amount of the hydroperoxide to a stoichiometric excess of the olefin, in a batch reaction either by heating a mixture of the components to reaction temperature or by incrementally adding the hydroperoxide to an excess of the olefin. The prior art also suggests the epoxidation of olefins using a substantial excess of the olefin in a continuous reaction by adding the hydroperoxide at spaced points to a stream of the olefin in an elongated reactor.

We have unexpectedly discovered that if barium oxide is present in the reaction mixture, the catalytic epoxidation of olefins with organic hydroperoxides can be successfully carried out with good selectivity to the epoxide based on hydroperoxide converted when the olefin is incrementally added to the reactor containing the hydroperoxide. That is, we have discovered by our invention that good selectivity to epoxide can be obtained at relatively low, instantaneous olefin to hydroperoxide mol ratios in the reaction zone which occur in our process during a substantial portion of the reaction time. We have further discovered that the selectivity of the hydroperoxide to the oxirane compound as well as the yield of the oxirane compound is surprisingly increased when barium oxide is used to stabilize the excess hydroperoxide in contrast with the conventional or regular procedure in which unstabilized hydroperoxide is added to an excess of the olefin. U.S. Pat. No. 3,351,635 states that it is advantageous for improved efficiency to employ basic substances, generically describing a large number of such basic substances, in the conventional epoxidation procedure described therein, presumably to neutralize acidic materials present as impurity in the hydroperoxide. Surprisingly, the process of our invention results in a conversion of hydroperoxide and its selectivity to the epoxide which is superior to the conventional epoxidation procedure, as described in this patent, with barium oxide present. Furthermore, the addition of the stable olefin to a stream of the unstable hydroperoxide at spaced points in an elongated reactor in accordance with our invention is the preferred industrial procedure for carrying out the epoxidation reaction.

In our invention the barium oxide stabilizes the hydroperoxide against undesired decomposition by the oxygen transfer catalyst when there is not sufficient olefin present in the reactor to prevent an extensive decomposition of the hydroperoxide, thereby permitting substantially all of the hydroperoxide oxygen to go to the olefin oxide. We believe that this effect of barium oxide is unique. Thus, we have determined that the improved yield of the olefin oxide is not a function of the barium moiety since other barium compounds do not produce the desired effect. Also we have tried many other basic substances for this purpose and found that no other basic material effectively stabilizes the hydroperoxide against undesired decomposition when it is present in the reactor in excess with respect to the olefin in the presence of the epoxidation catalyst. The data suggest that barium oxide is uniquely advantageous because it functions in a way or ways not limited to neutralization of impurities in the hydroperoxide.

Our process in general relates to the epoxidation of olefins under conditions which include an amount of olefin in the reactor during reaction which is normally insufficient to prevent a substantial decomposition of the organic hydroperoxide in the absence of barium oxide. A preferred method of carrying out the invention involves a batch operation in which the olefin and oxygen transfer catalyst are incrementally added, preferably in admixture, to a mixture of the hydroperoxide and the barium oxide. However, our reaction can be advantageously carried out, particularly for commercial production, in a continuous reaction by adding the olefin and epoxidation catalyst at from 2 up to 20 or more spaced points to a stream of the hydroperoxide and barium oxide mixture in an elongated reactor. This represents an incremental addition for the continuous process. Since the epoxidation reaction is highly exothermic, an incremental addition is used for the reaction to permit dissipation of the heat of the reaction.

By incremental addition we mean the addition or metering in over a finite period of time in contrast with the dumping of the total amount of the reactant into the reactor at one time. The term incremental addition includes addition using a continuous stream, addition using a variable stream, addition intermittently using separate portions, and any other related method provided that addition of the olefin is carried out over a finite, significant period of time, such as at least about 10 minutes in a batch reaction or at spaced points along an elongated reactor in a continuous reaction. Thus, in this incremental addition of the olefin to the hydroperoxide there will be a substantial excess of hydroperoxide as compared with the olefin present in the reactor until the hydroperoxide is substantially exhausted. The olefin can then be added in excess to the reaction zone, if desired, to insure substantially complete utilization of the hydroperoxide.

The process of adding the olefin to the hydroperoxide is particularly advantageous because it substantially simplifies the overall operation of producing the epoxide. By using this process a hydroperoxide can be produced in a reactor and then the olefin and oxygen transfer catalyst can be incrementally added to the hydroperoxide and barium oxide mixture in the same reactor to produce the epoxide. This represents a substantial reduction in expense because only one reactor is needed and the care required for the handling of the hydroperoxide is avoided. Otherwise, according to the conventional method, the hydroperoxide must be made in a first reactor, cooled to prevent decomposition of the hydroperoxide during transfer, and then added to the olefin in a second reactor in a batch reaction or added at spaced points in an elongated reactor to a flowing stream of the olefin in a continuous reaction. In large scale operations the excessive handling of hydroperoxide is hazardous and should be avoided. Another particular advantage of our invention is the ability of our process to use high concentrations of hydroperoxide with high conversion and high selectivity to the epoxide whereby very effective and economical utilization of the reactants and equipment is obtained.

This invention is particularly useful for the epoxidation of alpha-olefins, preferably those having from three to about 30 carbon atoms, and more preferably from three to about 20 carbon atoms. Olefins that are suitable herein include propylene, 1-butene, isobutene, 1-pentene, the methyl 1-pentenes, 1-hexene, 1-octene, 1-dodecene, 1-eicosene, butadiene, styrene, methyl styrene, vinyl toluene, vinyl pyridine, 2-ethyl-1-hexene, and the like. Alpha-olefins having substituents such as halogen, hydroxy, carbonyl, sulfur, ether, cyano, and the like containing substituents can also be conveniently epoxidized by the procedure described herein. Examples of such substituted olefins are allyl alcohol, methallyl alcohol, diallyl ether, methyl vinyl ketone, acrolein, methacrolein, allyl chloride, acrylonitrile, methacrylonitrile, and the like.

Any suitable organic hydroperoxide reactant which is known to be useful for the epoxidation of olefins in the presence of an oxygen-transfer catalyst can be used herein. We particularly prefer to use the hydroperoxides of cumene, ethylbenzene, isobutane and isopentane.

In carrying out the invention sufficient barium oxide is dispersed in the hydroperoxide solution to stabilize it against decomposition when the olefin and the epoxidation catalyst are added to this hydroperoxide solution. The hydroperoxide solution is the hydroperoxide in solution with the hydrocarbon from which it is formed such as ethylbenzene hydroperoxide and ethylbenzene together with any by-products from the oxidation reaction and impurities which do not significantly interfere with the desired reaction. The initial hydroperoxide concentration can be as high as 80 weight percent of the hydroperoxide solution. We prefer that this initial concentration of hydroperoxide in the hydroperoxide solution be from about 10 to about 50 weight percent. Although any concentration of barium oxide in the hydroperoxide is better than none at all, we find that from about 0.0001 to about 2.0 weight percent barium oxide based on the total organic hydroperoxide that may be present is satisfactory with a range of about 0.001 to about 0.40 weight percent being preferred.

Any suitable metal catalyst that is known to catalyze the oxygen transfer reaction can be used for the reaction herein. We prefer to use a soluble molybdenum compound such as molybdenum naphthenate, molybdenum acetylacetonate, molybdenum carbonyl, molybdenum halides such as molybdenum chloride and oxychloride, molybdenum phosphate, phosphomolybdic acid, the sodium salt thereof and the like as the catalyst. This oxygen transfer catalyst is conveniently used in a range of about 0.02 to about five weight percent and preferably about 0.05 to about 2.5 weight percent of the total amount of olefin, organic hydroperoxide and its precursor that is present, however, the oxygen transfer catalyst produces a catalytic effect even in trace amounts. The ratio of the catalyst to the barium oxide determined as the gram atoms of the catalyst metal per mol of barium oxide that is found to be suitable is between about 0.01:1 to about 10:1 and preferably between about 0.1:1 and about 5:1. Since the oxygen transfer catalyst catalyzes the decomposition of the hydroperoxide, it is not contacted with the hydroperoxide until it is needed for the epoxidation reaction. Therefore, the oxygen transfer catalyst is added to the hydroperoxide concurrently with the olefin, preferably in solution in the olefin.

The epoxidation reaction is carried out at a temperature between about 80° and about 150° C. and preferably between about 100° and about 130° C. The reaction is preferably carried out with the substantial elimination of free oxygen, since the presence of a significant amount of free oxygen tends to induce a reduction in the selectivity to the epoxide. An atmosphere can be present such as olefin vapor and/or nitrogen, helium, argon, methane, a paraffin such as the paraffin corresponding to the olefin, and the like. When propylene is the olefin, it is convenient to use a propylene-propane mixture as the feed stream, both of which can then be present in the reactor atmosphere. The reaction can be carried out without an atmosphere or gas phase such as in a continuous reactor.

DESCRIPTION OF PREFERRED EMBODIMENTS

In the following experiments the hydroperoxide was analyzed by iodometric titration with sodium thiosulfate and the epoxide content was determined by gas chromatography. As used herein, room temperature means a temperature of about 20°–25° C.

EXAMPLE 1

In a typical oxidation run to prepare cumene hydroperoxide, a mixture of 50 ml. cumene and 0.2 g. BaO was heated to 110° C. in a reactor. To this mixture was added 1 ml. cumene hydroperoxide as an initiator. Oxygen was bubbled through the reaction mixture at a rate of 100 cc./min. After five hours, the concentration of cumene hydroperoxide (CHP), as determined by standard iodometric titration, was 44 weight percent.

A solution of 18 percent ethylbenzene hydroperoxide in ethylbenzene was prepared by air oxidation of ethylbenzene using 4.5 percent ethylbenzene hydroperoxide as an initiator at 135° C. and 140 psi. air pressure for three hours.

EXAMPLE 2

A 50 ml. solution of 13 weight percent cumene hydroperoxide in cumene and containing 0.2 g. BaO was prepared as described in Example 1 after one hour of reaction. The oxygen was then flushed out with nitrogen and a nitrogen blanket was maintained in the reactor. A 20 ml. sample of 1-octene at about 25° C. containing 0.5 g. of molybdenum naphthenate (4.6 weight percent Mo) was then introduced in 25 minutes in a continuous stream while the reactor temperature was maintained at 120° C. Although better than 90 percent of the cumene hydroperoxide had reacted by the end of its addition, the reaction was run for a total of three hours in an effort to increase the conversion. The reaction mixture was cooled to room temperature and a small sample was again titrated iodometrically to determine the final CHP concentration. A 91 percent conversion of CHP was obtained. The selectivity to 1-octene oxide based on the CHP converted was 95 percent for an overall yield of about 86 percent.

EXAMPLE 3

A 50 ml. solution containing 13 weight percent cumene hydroperoxide was prepared by diluting with cumene a commercially pure solution of 85 percent cumene hydroperoxide in cumene. The 13 percent and 85 percent cumene hydroperoxide solutions are stable below 65° C. and can be stored for long periods at room temperature. To this 13 percent cumene hydroperoxide solution was added 0.2 g. of BaO and the mixture was heated to 120° C. under a $N_2$ atmosphere. A 20 ml. sample of octene-1 at about 25° C. containing 0.5 g. of molybdenum naphthenate was added in a continuous stream in one hour to the cumene hydroperoxide solution at 120° C. The mol ratio of cumene hydroperoxide to barium oxide was 35:1 and the mol ratio of the molybdenum catalyst to barium oxide was 0.2:1. The reaction mixture was maintained at 120° C. for two hours after the addition was completed. The reaction mixture was then cooled to 10° C. and analyzed. An 89 percent conversion of cumene hydroperoxide was obtained and the selectivity of the converted cumene hydroperoxide to 1-octene oxide was determined to be 93.5 percent for all overall yield of about 83 percent.

EXAMPLE 4

The results in Examples 2 and 3 are compared with the identical reaction using the conventional order of addition, that is, by metering the hydroperoxide into the olefin. A 50 ml. solution containing 13 percent cumene hydroperoxide was prepared by diluting with cumene a commercially pure solution of 85 percent cumene hydroperoxide in cumene. This cumene hydroperoxide solution, at about 25° C., was added at a constant rate over a one-hour period to a solution containing 20 ml. of 1-octene, 0.5 g. molybdenum naphthenate and 0.2 g. of barium oxide (BaO) maintained at 120° C. under a nitrogen atmosphere. The reaction mixture was maintained at a temperature of 120° C. for two hours after the addition was completed. The reaction mixture was then cooled to 10° C. and analyzed. A 75 percent conversion of cumene hydroperoxide was obtained and the selectivity of the converted cumene hydroperoxide to 1-octene oxide was determined to be 67 percent for an overall yield of about 50 percent.

EXAMPLE 5

Example 2 was repeated except that no BaO was used. The conversion of CHP was almost quantitative but only nine percent 1-octene oxide was formed. The results of Examples 2 through 5 are set out in Table I.

Table I

|              | Ex. 2 | Ex. 3 | Ex. 4[a] | Ex. 5 |
|---|---|---|---|---|
| BaO, wt. %   | 0.2   | 0.2   | 0.2   | 0     |
| Conversion   | 91    | 89    | 75    | 100   |
| Selectivity  | 95    | 93.5  | 67    | 9     |
| Yield        | 86    | 83    | 50    | 9     |

[a]cumene hydroperoxide metered into 1-octene

EXAMPLE 6

Example 2 was repeated except that the epoxidation was made under air atmosphere instead of nitrogen atmosphere. The conversion of CHP was almost quantitative but the selectivity to 1-octene oxide was 21 percent.

EXAMPLE 7

A series of runs were made to compare the stabilizing effect of barium oxide with a number of other materials as potential stabilizing additives. These runs were carried out by adding (over 20 to 30 minutes) 0.127 mol (20 ml.) 1-octene containing one weight percent (0.5 g.) molybdenum naphthenate to a 13 weight percent solution of cumene hydroperoxide containing the potential stabilizer under test. Each experiment was run at 120° C. under a non-oxidizing atmosphere. The results of these runs are set forth in Table II which shows the total reaction time and the conversion of cumene hydroperoxide (CHP) and its selectivity to 1-octene oxide.

Table II

| Additive | Wt.%[a] | mol Kg.[a] | Time, hrs. | CHP Conv.% | Select., % |
|---|---|---|---|---|---|
| None     | —    | —     | 1.0  | 100 | 9    |
| Charcoal | 0.30 | 0.250 | 0.1  | 100 | <1   |
| BaO      | 0.30 | 0.020 | 3.0  | 91  | 95   |
| $BaO_2$  | 0.30 | 0.018 | 1.0  | 100 | 12   |
| $Ba(OH)_2$ | 0.34 | 0.020 | 1.33 | 100 | 22.5 |
| NaOH     | 0.30 | 0.075 | 1.25 | 75  | 3.7  |
| KOH      | 0.30 | 0.055 | 1.5  | 76  | 3.9  |
| MgO      | 0.30 | 0.075 | 0.5  | 100 | 17   |
| MgO      | 0.08 | 0.020 | 1.0  | 100 | 11   |
| CaO      | 0.30 | 0.052 | 0.75 | 100 | 8    |
| $Ca(OH)_2$ | 0.16 | 0.020 | 1.5  | 100 | 23   |
| SrO      | 0.30 | 0.030 | 1.25 | 98  | 41   |
| ZnO      | 0.30 | 0.037 | 0.1  | 100 | 10.5 |
| ZnO      | 0.16 | 0.020 | 1.0  | 100 | 10.5 |
| NiO      | 0.30 | 0.040 | 1.0  | 100 | 5    |
| $MnC_2O_4$ | 0.30 | 0.020 | 0.5  | 100 | <1   |

[a]based on total reaction mixture

The unsuccessful run with charcoal indicates that the effect of barium oxide is not a surface effect. The fact that $Ba(OH)_2$ and $BaO_2$ are not successful indicates that the beneficial results do not result from barium per se.

EXAMPLE 8

A series of runs were made at 120° C. in which a mixture of 1-octene and molybdenum naphthenate was added to a 100 ml. flask containing various concentrations of cumene hydroperoxide in cumene under a nitrogen atmosphere having powdered barium oxide dispersed therein. The addition was made over a period of 15 to 45 minutes depending on the amount of olefin added. The reaction was carried out for a total of two hours, although better than 90 percent of the reaction was completed at the end of the olefin addition. The amount of the two reactants and the two catalysts was varied and the effects on CHP conversion and selectivity to 1-octene oxide are recorded in Table III.

Table III

| CHP Wt.% | CHP Mols | BaO Wt.% | Mo-Naph. Wt.% | $C_8^=$, mols | % CHP Conv. | Select. % | %$C_8^=$, Conv. |
|---|---|---|---|---|---|---|---|
| 5.3 | 0.017 | 0 | 0.25 | 0.127 | 100 | 0 | 0 |
| 7.0 | 0.023 | 0.1 | 0.25 | 0.127 | 100 | 87 | 16 |
| 13.0 | 0.043 | 0.3 | 1.0 | 0.063 | 92 | 65 | 40 |
| 12.8 | 0.042 | 0.3 | 1.0 | 0.127 | 91 | 95 | 28 |
| 20.7 | 0.068 | 0.3 | 2.0 | 0.127 | 97 | 68 | 35 |
| 22.3 | 0.073 | 0.4 | 3.0 | 0.255 | 100 | 92 | 26 |
| 27.1 | 0.089 | 0.3 | 2.0 | 0.127 | 100 | 47 | 33 |
| 42.7 | 0.014 | 0.4 | 3.0 | 0.255 | 95 | 23 | 12 |
| 41.3 | 0.136 | 0.3 | 2.0 | 0.510 | 100 | 76 | 20 |

EXAMPLE 9

A 50 ml. solution containing 13 percent cumene hydroperoxide was prepared as described in Example 3. To this cumene hydroperoxide solution was added 0.2 g. of BaO and the mixture was heated to 120° C. under a $N_2$ atmosphere. A 20 ml. sample of 2-ethyl-1-hexene at about 25° C. containing 0.5 g. of molybdenum naphthenate was added in one hour to the cumene hydroperoxide solution at 120° C. The reaction mixture was maintained at 120° C. for two hours after the addition was completed. The reaction mixture was then cooled and analyzed. A 99 percent converstion of cumene hydroperoxide was obtained and the selectivity of the converted cumene hydroperoxide to 2-ethyl-1-hexene oxide was determined to be 94.0 percent for an overall yield of about 93 percent.

EXAMPLE 10

A solution of 18 weight percent ethylbenzene hydroperoxide in ethylbenzene was prepared by air oxidation of ethylbenene at 135° C. and 140 psi. air pressure using 4.5 percent ethylbenzene hydroperoxide as an initiator. A 50 cc. (46.0 g.) portion of this ethylbenzene hydroperoxide solution was placed in a 100 cc. glass reactor and heated to 110° C. The oxygen was flushed out of the reactor with nitrogen and a nitrogen blanket was maintained in the reactor. A 20 cc. (14.5 g.) sample of 1-octene at about 25° C. and containing 2.5 g. of molybdenum naphthenate (2.0 weight percent Mo) was slowly charged to the reactor over 20 minutes while the reaction temperature was maintained at 110° C. The catalyst was 0.08 weight percent of the total solution of ethylbenzene, ethylbenzene hydroperoxide and 1-octene. After running the reaction for a total of one hour, the reaction mixture was cooled to room temperature and its final ethylbenzene hydroperoxide and octene oxide content was determined. A 97.6 percent conversion of ethylbenzene hydroperoxide was obtained. The selectivity to 1-octene oxide based on the ethylbenzene hydroperoxide converted was 21.0 percent for an overall yield of 20.5 percent.

EXAMPLES 11-14

Example 10 was repeated in a series of experiments except that varying amounts of dry powdered barium oxide were added to the ethylbenzene hydroperoxide (EBHP) solution. The results of these experiments are set out in Table IV. The conversion is the conversion of the ethylbenzene hydroperoxide and the selectivity is the amount of 1-octene oxide divided by the amount of ethylbenzene hydroperoxide converted.

Table IV

| Example | 10 | 11 | 12 | 13 | 14 |
|---|---|---|---|---|---|
| BaO,wt.% | 0 | 0.016 | 0.024 | 0.032 | 0.048 |
| $\frac{Mo}{BaO}$ (mol) | — | 3.6 | 2.4 | 1.8 | 1.2 |
| $\frac{EBHP}{BaO}$ (mol) | — | 700 | 467 | 350 | 233 |
| Time,hrs. | 1.0 | 1.0 | 1.5 | 2.0 | 2.0 |
| Conversion% | 97.6 | 99.0 | 97.4 | 80.0 | 9.6 |
| Selectivity% | 21.0 | 60.6 | 69.5 | 61.3 | 89.4 |
| Yield% | 20.5 | 60.0 | 67.7 | 49.0 | 8.6 |

EXAMPLE 15

The same components and quantities that were used in Example 10 were used in this experiment, except that a prior art procedure was used. The ethylbenzene hydroperoxide solution was slowly added to the 1-octene and catalyst solution at 110° C. over a period of 20 minutes. After one hour from the start of the addition, 98.7 percent of the hydroperoxide was converted with a selectivity to 1-octene oxide of 41.0 percent and a yield of the epoxide of 40.4 percent.

EXAMPLE 16

The same components and quantities that were used in Example 10 were used in this experiment, except that another prior art procedure was used. The ethylbenzene hydroperoxide and the 1-octene were mixed together at room temperature (about 20° C.) and heated up to 110° C. in less than 20 minutes. After one-half hour at 110° C., the reaction mixture was cooled to room temperature. It was determined that 99 percent of the ethylbenzene hydroperoxide was converted at a selectivity to 1-octene oxide of 21.0 percent and a yield of the epoxide of 20.7 percent.

EXAMPLE 17

The procedure in Example 12 was followed except that 20 cc. (13.5 g.) of 1-hexene was charged in 20 minutes to the reactor containing 50 cc. of 18 weight percent ethylbenzene hydroperoxide at a reactor temperature of 100° C. After a total time of one and one-half hours, the reaction mixture was cooled to room temperature and analyzed. A conversion of 94.3 percent of the hydroperoxide was obtained at a selectivity of 72.5 percent based on the ethylbenzene hydroperoxide converted at an overall yield of 68.4 percent.

EXAMPLES 18-22

A series of experiments were carried out using the same procedures, compositions and amounts as used in Example 12 except that 0.024 weight percent of other Group IIA basic substances and sodium naphthenate were used. The overall reaction time is set out in Table V:

Table V

| Example | 12 | 18 | 19 | 20 | 21 | 22 |
|---|---|---|---|---|---|---|
| Base | BaO | SrO | CaO | MgO | $MgCO_3$ | NaNaph. |
| Time,hrs. | 1.5 | 1.0 | 1.0 | 1.5 | 1.0 | 1.5 |
| Conv.% | 97.4 | 92.8 | 98.2 | 96.9 | 96.8 | 77.7 |
| Select.% | 69.5 | 43.0 | 37.9 | 47.4 | 44.0 | 33.7 |
| Yield% | 67.7 | 39.9 | 37.2 | 45.9 | 42.6 | 26.2 |

EXAMPLE 23

The epoxidation of propylene with ethylbenzene hydroperoxide was carried out in a 300 ml. stainless steel autoclave at 110° C. and 400 psi. (3000 kPa) nitrogen pressure to keep the propylene in the liquid phase. A 50 mg. portion of powdered, anhydrous barium oxide and 100 ml. of 18 weight percent solution of ethylbenzene hydroperoxide in ethylbenzene was charged to the reactor. The reactor is flushed and pressured with nitrogen to 400 psi. and is heated to 110° C. with stirring. A total quantity of 30 g. of propylene (0.255 mol) containing 0.45 weight percent $Mo(CO)_6$ is pumped as a uniform stream into the reactor over a period of about five minutes. After maintaining the pressure for about 30 minutes, the reactor is cooled and the product is analyzed. The results are set out in Table VI.

EXAMPLES 24–27

The procedures, compositions and quantities of Example 23 were repeated except that the amount of barium oxide was varied. The conversion of ethylbenzene hydroperoxide and the selectivity and yield to propylene oxide are shown in Table VI.

Table VI

| Example | 23 | 24 | 25 | 26 | 27 |
|---|---|---|---|---|---|
| BaO, mg. | 50 | 75 | 100 | 150 | 0 |
| Weight % | 0.04 | 0.06 | 0.08 | 0.12 | 0 |
| $\frac{EBHP}{BaO}$ (mol) | 380 | 570 | 760 | 1140 | — |
| $\frac{Mo}{BaO}$ (mol) | 1.56 | 2.34 | 3.12 | 4.68 | — |
| Conversion % | 98.4 | 96.3 | 95.4 | 91.8 | 99.0 |
| Selectivity % | 75.5 | 81.0 | 82.0 | 83.9 | 61.5 |
| Yield % | 74.4 | 78.1 | 78.2 | 77.0 | 60.9 |

EXAMPLE 28

This experiment demonstrates the conventional procedure for making propylene oxide from ethylbenzene hydroperoxide and propylene. The 300 ml. stainless steel autoclave was charged with 100 ml. of the 18 percent solution of ethylbenzene hydroperoxide at room temperature. The air was replaced with dry nitrogen. At room temperature, 30 g. of propylene containing 0.45 weight percent $Mo(CO)_6$ is charged to the reactor. The autoclave is heated to 110° C. with stirring and is pressured to 400 psi. with dry nitrogen. After heating at 110° C. for 30 minutes, the reactor is cooled and its contents analyzed. It was determined that there was 99 percent conversion of the ethylbenzene hydroperoxide at a selectivity to propylene oxide of 69.8 percent and yield of 69.3 percent.

EXAMPLES 29–32

The procedures of Example 23 are repeated using 100 ml. of 35 percent ethylbenzene hydroperoxide in ethylbenzene and 60 g. of propylene containing 0.45 percent $Mo(CO)_6$. The propylene is pumped into the ethylbenzene hydroperoxide solution containing the base at a temperature of 110° C. and under a pressure of 400 psi. over a period of five minutes. The contents of the reactor are heated for 30 minutes after the propylene has been added and are then cooled and analyzed. The results are set out in Table VII.

Table VII

| Example | 29[a] | 30 | 31 | 32 |
|---|---|---|---|---|
| BaO, g. | 0.05 | 0.1 | 1.0 | 0[b] |
| Weight % | 0.04 | 0.08 | 0.80 | 0 |
| Conversion % | 98.6 | 92.4 | 18.8 | 96.2 |
| Selectivity % | 78.6 | 83.6 | 83.3 | 72.3 |
| Yield % | 77.5 | 77.3 | 15.7 | 69.6 |

[a] average of two runs.
[b] 0.08 wt. % sodium naphthenate was used in place of barium oxide.

EXAMPLE 33

The procedures of Example 28, which involved the conventional method for making olefin oxides, were repeated except that 100 ml. of a solution of 35 percent ethylbenzene hydroperoxide in ethylbenzene and 60 g. of propylene containing 0.45 percent $Mo(CO)_6$ were used. Analysis of the products obtained by the thirty-minute heating at 110° C. revealed that there was 99.3 percent conversion of the ethylbenzene hydroperoxide at a selectivity of 70.8 percent and yield of 70.3 percent to propylene oxide.

EXAMPLE 34

The procedures, compositions and quantities of Example 33, involving the prior art techniques, were repeated except that 50 mg. (0.04 wt.%) barium oxide was present in the reactor before the propylene was added. The product was analyzed after heating at 110° C. for 30 minutes. The conversion of ethylbenzene hydroperoxide was 97.6 percent at a selectivity of 69.7 percent and yield of 68.0 percent to propylene oxide.

EXAMPLE 35

The 300 ml. stainless steel autoclave was charged with 100 ml. of 18 percent ethylbenzene hydroperoxide and 11.5 mg. of powdered, anhydrous barium oxide. After flushing and pressuring the reactor with dry nitrogen to 400 psi., the reactor is heated to 110° C. A steady stream of propylene containing 0.23 weight percent molybdenum naphthenate and four weight percent acetophenone to prevent the precipitation of molybdenum naphthenate is pumped into the reactor. A total quantity of 30 g. of propylene is added in 10 minutes. The amount of barium oxide in the reactor was 0.01 weight percent of the total reaction liquid. The reactor was maintained at 110° C. After 30 minutes from the start of the propylene addition, there was 80 percent conversion of the hydroperoxide at a selectivity of 80 percent to propylene oxide. After one hour from the first addition of propylene oxide, analysis of the reaction liquid revealed that 87 percent of the ethylbenzene hydroperoxide had been converted, at a selectivity to propylene oxide of 82 percent and a yield of propylene oxide of 71.4 percent.

After maintaining a reactor temperature of 110° C. for an additional hour, the contents of the reactor were again analyzed. This analysis disclosed a conversion of ethylbenzene hydroperoxide of 94 percent and a selectivity and yield of 81 and 76 percent, respectively.

EXAMPLE 36

The procedures, components and quantities of Example 35 were repeated except that 4.0 mg. of barium oxide (0.003 percent) were present in the reactor. The analysis after 30 minutes showed a conversion of 89 percent and a selectivity of 73 percent. The analysis after one hour disclosed a conversion of ethylbenzene hydroperoxide of 94 percent at 78 percent selectivity and 72.5 percent yield of propylene oxide.

EXAMPLE 37

In this experiment the conventional procedure was further demonstrated. The 300 ml. stainless steel autoclave was charged with 100 ml. of 18 percent ethylbenzene hydroperoxide in ethylbenzene. The reactor was flushed with dry nitrogen and 30 g. of propylene containing 0.23 weight percent molybdenum naphthenate and 4.0 weight percent acetophenone were added at room temperature. The autoclave was pressured to 400 psi. with dry nitrogen and heated to 110° C. for one hour. An analysis was made 30 minutes from the start of the propylene addition showing that the conversion of hydroperoxide was 78 percent at a selectivity of 64 percent to propylene oxide. Analysis of the reaction product showed that 99 percent of the ethylbenzene hydroperoxide had been converted at a selectivity of 73 percent and yield of 72.3 percent to propylene oxide.

After continuing the heating of the contents of the reactor for an additional hour at 110° C., the conversion increased to 100 percent but the selectivity dropped to 65 percent.

EXAMPLE 38

A solution of 50 cc. of 17 weight percent tertbutyl hydroperoxide (t.BHP) was prepared by mixing 14 cc. of commercial 70 percent t.BHP in isobutane with 36 cc. of xylene. This solution and 0.5 g. of molybdenum naphthenate (2.0 weight percent Mo) was charged into a 100 cc. glass reactor. The oxygen in the reactor was flushed out with nitrogen and a nitrogen blanket was maintained in the reactor. The reactor was then placed in an oil-bath and heated to 105° C. for two hours. During the two hours, a small sample was periodically taken from the reactor and was titrated iodometrically to determine the t.BHP concentration. The results are shown in Table VIII.

The decomposition of t.BHP was also carried out using the same solution and procedure except that 0.2 g. of dry, powdered BaO was also charged to the reactor (0.4 weight percent) to stabilize the t.BHP. The results are also shown in Table VIII.

Table VIII

| Time, min. | t.BHP conc.% | | %Decomposition | |
|---|---|---|---|---|
| | 0%BaO | 0.4%BaO | 0%BaO | 0.4%BaO |
| 0 | 16.2 | 16.4 | — | — |
| 30 | 14.6 | 16.0 | 9.8 | 2.4 |
| 60 | 7.1 | 14.3 | 56 | 12.8 |
| 120 | 2.9 | 13.7 | 82 | 16.5 |

The results demonstrate the unique effect of barium oxide in reducing the rates of t.butyl hydroperoxide decomposition by molybdenum naphthenate.

EXAMPLES 39–43

Cumene hydroperoxide was used to oxidize 1-octene in the presence of varying amounts of barium oxide. A 50 ml. portion of 13 percent cumene hydroperoxide in cumene was placed in a 100 ml. stirred reactor and the powdered, anhydrous barium oxide was added. The reactor was flushed with nitrogen and a nitrogen atmosphere was maintained in the reactor. After heating the reactor to 120° C., 0.127 mol of 1-octene containing one percent molybdenum naphthenate was slowly charged to the reactor over a period of about 30 minutes. The reaction mixture was heated at 120° C. for a total of two hours and was then cooled and analyzed. The results are set forth in Table IX showing the conversion of cumene hydroperoxide and the selectivity of 1-octene oxide.

Table IX

| Example | 39 | 40 | 41 | 42 | 43 |
|---|---|---|---|---|---|
| BaO, wt.% | 0 | 0.05 | 0.20 | 0.30 | 0.40 |
| Conv.% | 100 | 100 | 100 | 100 | 65 |
| Select.% | 0 | 21 | 84 | 97 | 65 |

EXAMPLES 44–47

The procedure of Example 42 was followed using the same components and amounts except that varying amounts of molybdenum naphthenate were placed in the 1-octene. The results are set forth in Table X which sets out the concentration of molybdenum naphthenate in the 1-octene, the conversion of cumene hydroperoxide and the selectivity to 1-octene oxide.

Table X

| Example | 44 | 45 | 42 | 46 | 47 |
|---|---|---|---|---|---|
| MoNaph.% | 0.25 | 0.5 | 1.0 | 2.0 | 3.0 |
| Conv.% | 88 | 100 | 100 | 100 | 100 |
| Select.% | 3 | 63 | 97 | 79 | 44 |

EXAMPLES 48 AND 49

The procedure of Example 42 was followed using the same components and amounts except that varying amounts of 1-octene were used. The results are set out in Table XI which shows the amount of 1-octene used, the time of olefin addition, the conversion of cumene hydroperoxide and the selectivity to 1-octene oxide.

Table XI

| Example | 48 | 42 | 49 |
|---|---|---|---|
| 1-octene,mols | 0.064 | 0.127 | 0.255 |
| Addition time,min. | 30 | 40 | 55 |
| Conversion,% | 82 | 100 | 100 |
| Selectivity,% | 56 | 97 | 78 |

EXAMPLES 50–54

The procedure, components and amounts of Example 42 were repeated in a series of experiments except that the reaction was carried out at different temperatures. The results are set out in Table XII which sets forth the reaction temperature, the conversion of cumene hydroperoxide and the selectivity to 1-octene oxide.

Table XII

| Example | 50 | 51 | 52 | 42 | 53 | 54 |
|---|---|---|---|---|---|---|
| Temp. °C. | 85 | 100 | 110 | 120 | 130 | 140 |
| Conv.% | 92 | 97 | 100 | 100 | 100 | 100 |
| Select.% | 50 | 82 | 91 | 97 | 83 | 58 |

EXAMPLE 55

A solution of 0.021 mol of cumene hydroperoxide in 45 g. of cumene and containing 0.05 g. (0.3 weight percent based on total reactants) of barium oxide was heated to 120° C. under a nitrogen atmosphere. A second solution containing 20 ml. of 1-octene and 0.13 g. (0.06 weight percent) of molybdenum naphthenate (containing 4.6 percent Mo) was slowly added at a constant rate over a 30 minute period to the cumene hydroperoxide solution. Periodic analyses of the solution were made. After the addition of the 1-octene had been completed (30 minutes), more than 80 percent of the hydroperoxide had reacted. The results of these analyses are set out in Table XIII.

Table XIII

| Time, Min. | 1-octene added, ml. | CHP,% | CHP Conv.% |
|---|---|---|---|
| 0 | 0 | 6.4 | 0 |
| 15 | 10 | 3.1 | 52 |
| 30 | 20 | 1.2 | 81 |
| 60 | 20 | 0.6 | 91 |
| 80 | 20 | 0 | 100 |

The selectivity of the cumene hydroperoxide to octene oxide was determined to be 92 percent.

EXAMPLE 56

A 45 g. solution of cumene containing 22.3 weight percent cumene hydroperoxide with 0.2 g. of powdered barium oxide added was placed in a reactor under a nitrogen atmosphere and heated to 120° C. A second solution containing 1.5 g. molybdenum naphthenate (containing 4.6 percent Mo) in 40 ml. of 1-octene was slowly added to the first solution over a 60 minute period. Periodic analyses of the solution were made. After the addition of the 1-octene had been completed, more than 85 percent of the hydroperoxide had reacted. The results of these analyses are set out in Table XIV.

Table XIV

| Time, min. | CHP,% | CHP conv.% |
|---|---|---|
| 0 | 22.3 | 0 |
| 65 | 2.7 | 87.6 |
| 95 | 1.1 | 91.3 |
| 155 | 0.5 | 97.3 |
| 275 | 0 | 100 |

The selectivity of the cumene hydroperoxide to octene oxide was determined to be 91.8 percent.

EXAMPLE 57

Propylene is continuously converted to propylene oxide in a one and one-half inch I.D. stainless steel tube reactor five feet long and containing an inlet end and an outlet end and two equally spaced inlet ports. Hot, freshly prepared ethylbenzene hydroperoxide containing 20 percent ethylbenzene hydroperoxide in ethylbenzene and 0.055 weight percent barium oxide is charged to the inlet end of the reactor at a flow rate of 6.960 g. per hour. A 590 g. per hour stream of propylene at a pressure of 400 psi and containing 0.45 weight percent molybdenum hexacarbonyl is also introduced into the inlet end of the reactor. The reactor is operated at 110° C. and at a pressure of 400 psi. Separate streams of propylene, also containing 0.45 weight percent molybdenum hexacarbonyl, are introduced into each inlet port at a rate of 500 g. per hour. Analysis of the product recovered from the reactor shows a conversion of 95 percent and a selectivity of the hydroperoxide to propylene oxide of 75.5 percent.

When the reaction is repeated using the same conditions and flow rates without the use of barium oxide, the conversion is 78.8 percent and the selectivity is 39.2 percent.

In like manner, propylene and molybdenum acetylacetonate are incrementally added to a mixture of isobutane hydroperoxide and barium oxide, and propylene and molybdenum carbonyl are incrementally added to a mixture of isopentane hydroperoxide and barium oxide and in each instance the hydroperoxide is stabilized against undesired decomposition by the oxygen transfer catalyst and a more efficient utilization of the hydroperoxide is obtained than results in the conventional order of addition.

Since most organic hydroperoxides decompose nonselectively by a free-radical mechanism, it is believed that the barium oxide possesses the unique property of substantially reducing the nonselective decomposition of the hydroperoxide and enhancing the catalytic epoxidation of olefins. The barium oxide is not consumed in the reaction and only small concentrations are required. It is regarded as a co-catalyst, that is, a hydroperoxide stabilization catalyst. It is believed that free oxygen present in the reaction mixture accelerates the nonselective decomposition of the hydroperoxides and that the presence of a non-oxidizing atmosphere eliminates this undesired effect.

It is to be understood that the above disclosure is by way of specific example and that the numerous modifications and variations are available to those of ordinary skill in the art without departing from the true spirit and scope of the invention.

We claim:

1. The method of preparing an oxirane compound which comprises incrementally adding an alpha-olefinically unsaturated compound and concurrently incrementally adding a soluble molybdenum compound as an oxygen transfer catalyst to an organic hydroperoxide at a concentration of from about 10 to about 50 weight percent with the substantial elimination of free oxygen and at a temperature of from about 80° to about 150° C., said organic hydroperoxide selected from cumene hydroperoxide, ethylbenzene hydroperoxide, isobutane hydroperoxide and isopentane hydroperoxide, and said organic hydroperoxide containing sufficient barium oxide in admixture with the hydroperoxide to stabilize the hydroperoxide against decomposition.

2. The method of preparing an oxirane compound in accordance with claim 1 in which the hydroperoxide is ethylbenzene hydroperoxide.

3. The method of preparing an oxirane compound in accordance with claim 1 in which the temperature is about 100° to about 130° C.

4. The method of preparing an oxirane compound in accordance with claim 1 in which the hydroperoxide is isobutane hydroperoxide.

5. The method of preparing an oxirane compound in accordance with claim 1 in which the olefin is propylene.

6. The method of preparing an oxirane compound in accordance with claim 1 in which the oxygen transfer catalyst is molybdenum naphthenate.

7. The method of preparing an oxirane compound in accordance with claim 1 in which the oxygen transfer catalyst is molybdenum hexacarbonyl.

8. The method of preparing an oxirane compound in accordance with claim 1 in which there is between about 0.0001 and about 2.0 weight percent barium oxide based on the total hydroperoxide.

9. The method of preparing an oxirane compound in accordance with claim 1 in which the reaction is carried out in the presence of a trace to about five weight percent of the soluble molybdenum compound and the ratio of gram atoms of molybdenum to mols of barium oxide is between about 0.01:1 and about 10:1.

10. The method of preparing an oxirane compound in accordance with claim 1 in which the reaction is a batch reaction and the incremental addition is carried out over a period of at least about five minutes.

11. The method of preparing an oxirane compound in accordance with claim 1 in which the concentration of barium oxide is between about 0.001 and about 0.4 weight percent based on the total organic hydroperoxide.

12. The method of preparing an oxirane compound in accordance with claim 1 in which the alpha-olefinically unsaturated compound is an alpha-olefin having from three to about 30 carbon atoms; or an alpha-olefin having from three to about 30 carbon atoms having substituted thereon halogen, hydroxy, carbonyl, sulfur, ether or cyano.

13. The method of preparing an oxirane compound in accordance with claim 1 in which said hydroperoxide and said barium oxide are introduced as a stream into the inlet end of an elongated reactor and said olefin and said soluble molybdenum compound are introduced into said stream in said reactor at from two to about 20 spaced injection points.

14. The continuous method of preparing an oxirane compound in accordance with claim 13 in which there is between about 0.0001 and about 2.0 weight percent barium oxide based on the total hydroperoxide.

15. The continuous method of preparing an oxirane compound in accordance with claim 13 in which the reaction is carried out in the presence of a trace to about five weight percent of the soluble molybdenum compound and the ratio of gram atoms of molybdenum to mols of barium oxide is between about 0.01:1 and about 10:1.

16. The continuous method of preparing an oxirane compound in accordance with claim 13 in which the organic hydroperoxide is ethylbenzene hydroperoxide.

17. The continuous method of preparing an oxirane compound in accordance with claim 13 in which the olefin is propylene.

18. The continuous method of preparing an oxirane compound in accordance with claim 13 in which the concentration of barium oxide is between about 0.001 and about 0.4 weight percent based on the total organic hydroperoxide.

* * * * *